United States Patent [19]
Lee et al.

[11] Patent Number: 5,629,019
[45] Date of Patent: May 13, 1997

[54] FORMULATIONS WITH HYDROPHOBIC PERMEATION ENHANCERS

[75] Inventors: Eun Soo Lee, Redwood City; Su Il Yum, Los Altos; Michel J. N. Cormier, Mountain View, all of Calif.

[73] Assignee: ALZA Corporation, Palo Alto, Calif.

[21] Appl. No.: 64,689

[22] Filed: May 20, 1993

Related U.S. Application Data

[62] Division of Ser. No. 842,816, Feb. 27, 1992, abandoned.

[51] Int. Cl.$^6$ .............................................. A61K 9/06
[52] U.S. Cl. .................. 424/489; 424/449; 514/944; 514/946; 514/951
[58] Field of Search ............................. 424/489, 449, 424/448; 514/946, 951, 944

[56] References Cited

U.S. PATENT DOCUMENTS

| | | | |
|---|---|---|---|
| 4,746,515 | 5/1988 | Cheng et al. | 424/449 |
| 4,778,678 | 10/1988 | Guse et al. | 424/487 |
| 4,863,738 | 9/1989 | Taskovich | 424/449 |
| 4,882,163 | 11/1989 | Guse et al. | 424/448 |
| 4,946,853 | 8/1990 | Bannon et al. | 514/343 |

FOREIGN PATENT DOCUMENTS

| | | |
|---|---|---|
| 0496316 | 7/1992 | European Pat. Off. |
| 2098865 | 12/1986 | United Kingdom . |

OTHER PUBLICATIONS

Dialog Information Services, File 351, WPIL, Dialog Access. No. 008655304, WPI Acces. No. 91–159331/22, Yg Nonogawa Shoji: "Drug for extgernal dermal use–contains active drug, e.g. indomethacin, enveloped . . . ".

Dialog Information Services, File 155, Medline, Dialog Access. No. 07981724, Medline Access No. 92119724, Wearley LL: "Recent Progress in Protein and Peptide Delivery by Noninvasive Routes".

*Primary Examiner*—Jyothsna Venkat
*Attorney, Agent, or Firm*—Michael J. Rafa; Felissa H. Cagan; Steven F. Stone

[57] ABSTRACT

This invention is directed to a novel formulation for effectively utilizing hydrophobic permeation enhancers for the increased permeability of active agents through the skin or mucosa along with reduction of the lag time between application of the active agent and attainment of a therapeutically effective agent flux, with little or no irritation to the host. The invention is directed to compositions containing a hydrophobic permeation enhancer, which permeation enhancer has been micronized and stabilized in an inert carrier such as water. These compositions can be combined with a biologically active agent to provide enhanced permeability of the active agent to the skin or mucosa.

7 Claims, 2 Drawing Sheets

FORMULATIONS WITH HYDROPHOBIC PERMEATION ENHANCERS

This application is division of Ser. No. 07/842,816 filed Feb. 27, 1992, now abandoned.

FIELD OF THE INVENTION

This invention pertains to the transdermal delivery of active agents and more particularly to novel methods and compositions for improving the permeation activity of hydrophobic permeation enhancers.

BACKGROUND OF THE INVENTION

Certain compounds are known in the art for their ability to provide enhanced permeability of skin or other body surfaces to biologically active agents. However, when these permeation enhancers are hydrophobic, their true permeation enhancement effect is often not completely expressed in practical application due to their limited solubility in water. The low solubility leads to a slow dissolution rate of the permeation enhancers in the water. Since partitioning of the permeation enhancers into the skin is much controlled by the dissolution, it is a slow process and there can be a significant lag time between application and attainment of the desired active agent flux.

The problem with hydrophobic permeation enhancers can be solved by co-delivering a hydrophobic enhancer with a solvent carrier such as propylene glycol, ethanol, isopropyl alcohol or other small molecules which can solubilize the hydrophobic enhancers. However, with such solvents, irritation problems to the host are frequently encountered.

Therefore, despite the development of the art, there has remained a continuing need for improved techniques in the transdermal delivery of active agents with hydrophobic permeation enhancers.

SUMMARY OF THE INVENTION

It is therefore an object of the present invention to provide increased transport of an active agent across the skin or mucosa.

It is a further object of the invention to provide improved transdermal permeation activity of a hydrophobic permeation enhancer.

A still further object of the invention is to provide a formulation for the transdermal delivery of an active agent at a therapeutically effective rate.

Another object of the invention is to eliminate the lag time between application of an active agent formulation to the skin or mucosa and attainment of the desired therapeutically effective flux level.

Yet another object of the invention is to avoid skin irritation arising as a result of an active agent formulation containing a hydrophobic permeation enhancer.

These and other objects of the invention are addressed by the present invention which is directed to compositions which provide accelerated partitioning of hydrophobic permeation enhancers into the skin or mucosa while exhibiting little or no irritation to the skin. More particularly, the invention is directed to compositions containing a hydrophobic permeation enhancer, which permeation enhancer has been micronized and stabilized in an inert carrier such as water. These compositions can be combined with a biologically active agent to provide enhanced permeability of the active agent to the skin or mucosa.

The invention is also directed to active agent formulations containing and active agent together with a micronized hydrophobic permeation enhancer and having enhanced permeability to the skin or mucosa.

The invention is additionally directed to a system which comprises a carrier or matrix adapted to be placed in active agent- and permeation enhancer-transmitting relation to a selected skin or other body site. The carrier or matrix contains sufficient amounts of active agent and permeation enhancer to continuously coadminister to the site, over a predetermined delivery period, the active agent, in a therapeutically effective amount, and the hydrophobic permeation enhancer, in an amount effective to enhance the permeation of the skin to the active agent.

The invention is further directed to methods for making and using the compositions, the formulations and the systems of the invention.

BRIEF DESCRIPTION OF THE DRAWINGS

FIG. 2 shows the flux from one donor epidermis and FIG. 3 shows the flux from epidermis of another donor.

DETAILED DESCRIPTION OF THE INVENTION

Figure 1:
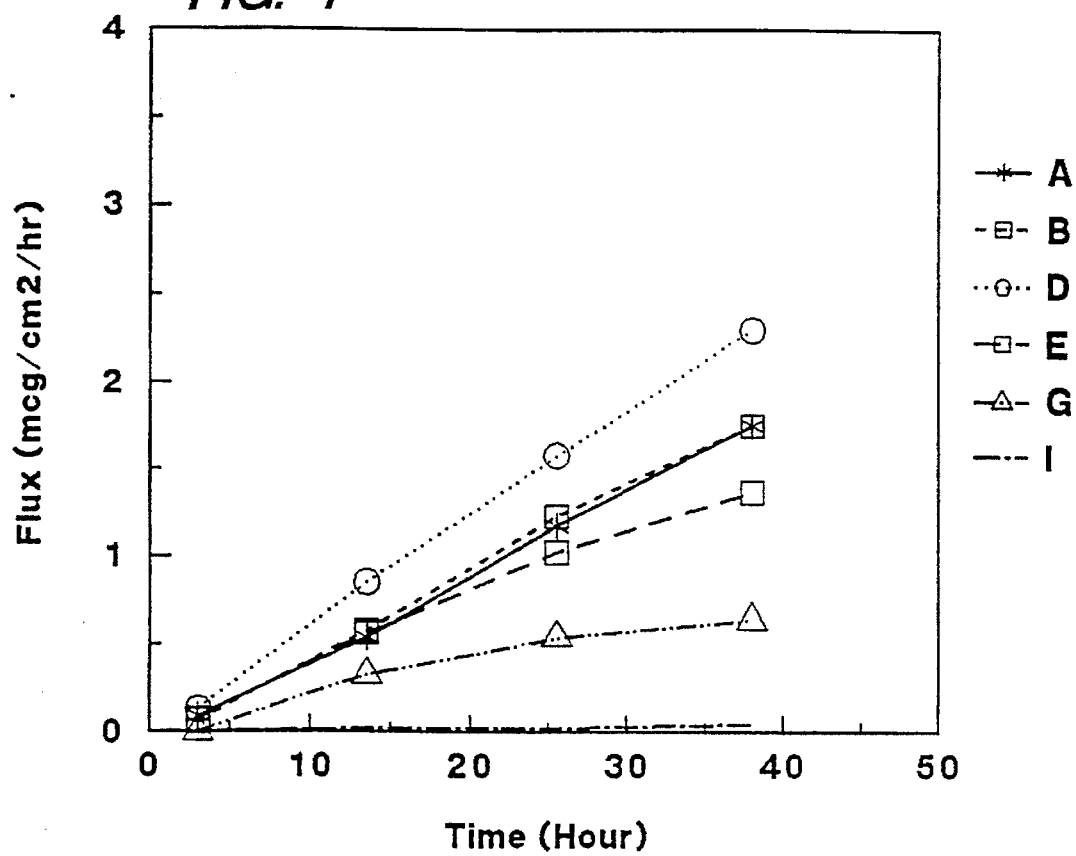
FIG. 1 is a graph showing the flux of hydrocortisone through epidermis from various glycerol monolaurate compositions falling under the present invention.

This invention utilizes principles of transdermal drug delivery to provide a novel formulation for effectively utilizing hydrophobic permeation enhancers for the increased permeability of active agents through the skin or mucosa along with reduction of the lag time between application of the active agent and attainment of a therapeutically effective agent flux, with little or no irritation to the host.

In order to accelerate the partitioning of hydrophobic permeation enhancers in non-solvent, inert carriers such as water, glycerol and polyethylene glycols with various molecular weights (such as PEG 400), it has been found by the inventors that the permeation enhancer can be micronized in the inert carrier to provide particles of from about 0.01 microns to about 1000 microns in diameter. These microparticles can then be stabilized by the addition of a stabilizing agent to provide a composition of micronized and stabilized hydrophobic permeation enhancer (the "permeation enhancer composition" of the invention). It has been found that when an active agent and this permeation enhancer composition are combined to make an active agent formulation according to the present invention, the active agent formulation surprisingly provides a greatly increased flux of the active agent with a reduction in the lag time as compared to a formulation utilizing a non-micronized hydrophobic permeation enhancer.

Without being bound by theory, it is believed that the micronization accelerates the skin partitioning of the permeation enhancer as a result of one, or possibly both, of two possible scientific grounds: an increased dissolution rate due to increased surface area of the permeation enhancer (the Noyes Whitney equation) or an increase of thermodynamic activity due to reduced particle size of the permeation enhancer (the Kelvin equation). The resulting accelerated skin partitioning increases the permeation activity of the enhancer while reducing or eliminating the lag time between application to the skin and attainment of a therapeutically effective flux rate. Additionally, because accelerated partitioning can occur in an inert carrier as a result of this invention., use of harmful solvents are not necessary and irritation to the host is therefore avoided.

In one embodiment of the present invention, the permeation enhancer composition of the invention is prepared by mechanically or otherwise micronizing a hydrophobic permeation enhancer in an inert carrier such as water by methods generally known in the art. The resulting microparticles of enhancer are from about 0.01 micron to about 1000 microns in diameter, preferably from about 0.1 micron to about 100 microns. A micronization stabilizing agent is then added to maintain the microparticles distributed throughout the carrier solution. Without the stabilizer, the microparticles will precipitate out of solution and the composition will lose its increased permeation-enhancing effectiveness.

Permeation enhancers which are useful in the present invention are those enhancers which are hydrophobic so that they are insoluble or only slightly soluble in water or other inert carriers. This includes, but is not limited to, fatty acids of from 10 to 20 carbon atoms, such as oleic acid, lauric acid, myristic acid, stearic acid, linoleic acid, and palmitic acid; mono-, di- and tri-glycerides of $C_{10-20}$ fatty acids, such as glycerol monolaurate, glycerol monooleate, glycerol dioleate, glycerol trioleate and glycerol monolinoleate; $C_{10-20}$ fatty acid mono-, di- and tri-esters of sorbitols, such as sorbitan monooleate, sorbitan trioleate, and sorbitan monolaurate; isopropyl myristate; sucrose monococoate; and the like. Glycerol monolaurate, glycerol monooleate, and glycerol monolinoleate are presently preferred. The hydrophobic permeation enhancer is present in the composition in a permeation-enhancing amount, that is, in an amount to effectively enhance the permeation of an active agent. This will depend on several factors, such as the particular active agent to be delivered but is generally in an amount of from about 0.1 wt % to about 50 wt %, preferably of from about 1 wt % to about 30 wt %.

The micronization stabilizer is hydrophilic and water soluble and may be selected from, but is not limited to, bile salts such as sodium deoxycholate, sodium cholate, sodium dehydrocholate, and the like; sodium laurate; sodium dodecylsulfate; sodium benzoate; sodium alginate; benzalkonium chloride; Tween 20; Tween 80; polyvinyl alcohol; and other ionic or nonionic surfactants with hydrophilic and lipophilic balance numbers greater than 15. The stabilizer is generally present in the composition in an amount of from about 0.1 wt % to about 5 wt %, preferably from about 0.2 wt % to about 3 wt %.

The inert carrier is preferably water, but may also be selected from, for example, glycerol and polyethylene glycols such as PEG 400.

The hydrophobic permeation enhancer composition of the present invention may be combined with a biologically active agent to provide enhanced transdermal delivery of the agent. As used herein, the term "transdermal" delivery or application refers to the delivery or application of agents by passage through skin, mucosa and/or other body surfaces by topical application. It is believed that this invention has utility in connection with the delivery of active agents within the broad class normally delivered through body surfaces and membranes, including the skin.

As used herein, the expression "active agent" is used interchangeably with the term "drug", and the two expressions are intended to have their broadest interpretation as to any therapeutically active substance, agent, drug, composition of matter or mixture thereof which is delivered to a living organism to produce a desired, usually beneficial, effect. In general, this includes therapeutic agents in all of the major therapeutic areas. Included among the types of agents which meet this description are biocides, sterilization agents, food supplements, nutrients, vitamins, sex sterilants, fertility inhibitors and fertility promoters. The agents include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, M. lipoproteins, polypeptides, steroids, analgesics, local anesthetics, antibiotic agents, anti-inflammatory corticosteroids, ocular drugs and synthetic analogs of these species.

Examples of beneficial agents with which this invention can be utilized are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, mectizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, pednisolone, 17-β-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, endlapriat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The active agent can be present in this invention in a wide variety of chemical and physical forms, such as uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations can be used. Derivatives such as esters, ethers and amides can be used. An active agent can be used alone or mixed with other active agents.

The lists of active agents recited above are given only to illustrate the types of active agents which are suitable for use in practicing the invention, and are not intended to be exhaustive.

The amount of active agent employed in the delivery device will be that amount necessary to deliver a therapeutically effective amount of the agent to achieve the desired result at the site of application. In practice, this will vary depending on the particular agent, the severity of the condition, and the desired effect, as well as the desired rate and duration of release.

The terms "therapeutically effective rate" and "therapeutically effective amount" as used herein mean a rate or an amount which provides a therapeutic effect or result.

The active agent and the micronized hydrophobic permeation enhancer are typically dispersed within a physiologically compatible matrix or carrier which may be applied directly to the body as an ointment, liquid, lotion, gel, cream, suppository or sublingual or buccal tablet, for example, or they may be administered from a matrix or carrier in a transdermal therapeutic delivery device. When used in the form of a liquid, ointment, lotion, cream or gel applied directly to the skin, it is often desirable although not required to occlude the site of administration to prevent evaporation of any volatile components. Such formulations can also contain other components of topical compositions as are known to the art. The formulations may also contain other optional components which enhance their cosmetic appeal or acceptability, such as thickeners, dyes, pigments, fragrances, perfumes, and the like.

Transdermal therapeutic devices for delivering a wide variety of drugs or other beneficial agents are well known in the art. Typical devices are described in U.S. Pat. Nos. 3,598,122, 3,598,123, 4,286,592, 4,314,557, 4,379,454, 4,559,222 and 4,573,995, for example. The coadministration of an active agent and a micronized hydrophobic permeation enhancer as disclosed herein can be accomplished using transdermal devices of these kinds.

In operation, the active agent formulation of the present invention is applied to an area of skin or mucosa as determined by the therapeutic result desired. If it is applied in an ointment, lotion or gel, for example, it is spread onto the area and it can be covered or occluded, although this is not required. If it is applied with a skin patch or other transdermal delivery device, the device is placed on the area of skin or mucosa and is held in place by an adhesive layer or overlay. Once the formulation is placed on the skin, it will begin coadministering the active agent and the permeation enhancer to the wearer so that the active agent is delivered in a therapeutically effective amount without irritation to the wearer.

While the active agent formulation can be administered to the skin or mucosa from a skin patch or other transdermal delivery device, it is preferably administered to skin or mucosa by direct application to the skin or mucosa in a carrier in the form of an ointment, gel, cream or lotion, for example. The formulation should be designed to deliver the active agent and the micronized hydrophobic permeation enhancer at the necessary release rates.

In a presently preferred embodiment of this invention, the active agent formulation is a cream. In addiition to the active agent, hydrophobic permeation enhancer, stabilizer and inert carrier, other additives may be included to provide an active agent cream with enhanced permeation activity. These additives include a humectant and a waxy oil.

The humectant may be selected from any of the known humectants which are compatible with the permeation enhancer and the active agent. These include, but are not limited to, glycerol, PEG400, propylene glycol, and the like. The humectant is generally present in the active agent formulation in an amount of from about 5 wt % to about 25 wt %.

The waxy oil may be selected from those generally known in the art and includes, but is not limited to, white petrolatum, fats, high molecular weight (i.e., solid or solid-like) organic alcohols, polyglycol esters, and the like. The oil phase is generally present in the active agent formulation in an amount of from about 10 wt % to about 60 wt %. This imparts stability and a smooth and velvety feel to the skin surface. It also assists in water retention.

Additionally, additives such as cetyl alcohol, stearyl alcohol or any other fatty alcohols may optionally be included in the oil phase to improve the creamy texture of the cream formulation.

When a constant drug delivery rate is desired, the active agent is present in the active agent formulation at a concentration at or in excess of saturation or solubility, the amount of excess being a function of the desired length of the agent delivery period. The active agent may, however, be present at a level below saturation without departing from this invention as long as the drug and the permeation enhancer are continuously and co-extensively administered to the same skin or mucosa site in an amount and for a period of time sufficient to obtain the desired therapeutic effect.

The following examples are offered to illustrate the practice of the present invention and are not intended to limit the invention in any manner.

EXAMPLE 1

A hydrocortisone formulation according to this invention was prepared as follows.

A first mixture of white petrolatum (35 wt %), glycerol monolaurate ("GML"; 15 wt %), glycerol (12 wt %) arid hydrocortisone (0.5 wt %) was heated in a water bath at 80°–85° C. with stirring until melted.

A second mixture, containing sodium deoxycholate (1.0 wt %) and water (36.5 wt %), was also heated separately in as water bath at 80°–85° C. with stirring until melted.

The two melts were then combined and allowed to cool, with constant stirring or shaking until the combined mixture was congealed, to give a hydrocortisone cream having contained therein a dispersion of micronized fine solid particles of glycerol monolaurate.

EXAMPLE 2

Following the procedure of Example 1, the formulations under Table A below were prepared (amounts are in wt %):

TABLE A

| ID. | GML | WPL | Glycerol | NaDC | Water | HCT |
|---|---|---|---|---|---|---|
| A | 10.0 | 0 | 0 | 0 | 89.5 | 0.5 |
| B | 15.0 | 0 | 0 | 0.5 | 84.0 | 0.5 |
| C | 10.0 | 0 | 0 | 0.5 | 89.0 | 0.5 |
| D | 7.5 | 0 | 0 | 0.5 | 91.5 | 0.5 |
| E | 5.0 | 0 | 0 | 0.5 | 94.0 | 0.5 |
| F | 2.5 | 0 | 0 | 0.5 | 96.5 | 0.5 |
| G | 0.5 | 0 | 0 | 0.5 | 98.5 | 0.5 |
| H | 0.25 | 0 | 0 | 0.5 | 98.75 | 0.5 |
| I | 0 | 0 | 0 | 0.5 | 99.0 | 0.5 |
| J | 25.0 | 25.0 | 12.0 | 1.0 | 36.5 | 0.5 |

GML = glycerol monolaurate
WPL = white petrolatum
NaDC = sodium deoxycholate
HCT = hydrocortisone

TABLE B

| ID. | Cumulative HCT Permeated ($\mu g/cm^2/46$ hr) |
|---|---|
| A | 47 |
| B | 49 |
| C | 45 |
| D | 65 |
| E | 40 |
| F | 34 |
| G | 20 |
| H | 8 |
| I | 1 |
| J | 70 |

While formulation A, without the sodium deoxycholate as a stabilizer, showed comparable flux to several other of the formulations, formulation A was unstable and the microparticles of GML settled out of solution and onto the bottom of the vessel. The formulations with NaDC all maintained their dispersion of micronized particles of GML regardless of the temperature or other environmental variables.

EXAMPLE 4

Various hydrocortisone cream formulations with different stabilizers were prepared following the procedures of Example 1. The formulations are given under Table C below (amounts are in wt %).

TABLE C

| | Cream Composition (%) | | | | | | | | | | |
|---|---|---|---|---|---|---|---|---|---|---|---|
| ID. | WPL | GML | Glycerol | SDS | Na-Benz. | Tween 20 | Na—Alg. | Benzalk. chl. | NaDC | Water | HCT |
| K | 35 | 15 | 12 | 1.0 | — | — | — | — | — | 36.5 | 0.5 |
| L | 35 | 15 | 12 | — | 1.0 | — | — | — | — | 36.5 | 0.5 |
| M | 35 | 15 | 12 | — | — | 2.0 | — | — | — | 35.5 | 0.5 |
| N | 35 | 15 | 12 | — | — | — | 0.34 | — | — | 37.16 | 0.5 |
| O | 35 | 15 | 12 | — | — | — | — | 1.0 | — | 36.5 | 0.5 |
| P | 30 | 20 | 12 | — | — | — | — | — | 1.0 | 36.5 | 0.5 |

WPL = white petrolatum
GML = glycerol monolaurate
SDS = Na dodecylsulfate
NaBenz = sodium benzoate
Na—Alg. = sodium alginate
NaDC = sodium deoxycholate
Benzalk. chl. = benzalkonium chloride
HCT = hydrocortisone

EXAMPLE 3

The hydrocortisone formulations A–J from Example 2 were tested in vitro to determine the flux of hydrocortisone across human cadaver epidermis at 35° C.

Test data were obtained using a 1.13 cm² wet-wet horizontal flux cell with 250 mg of donor solution and 20 ml of receptor solution (water). All donor formulations were saturated with the drug. The donor solution was removed and replaced periodically, and the transdermal flux and total drug permeated were measured. The transdermal flux of hydrocortisone for each formulation is shown in FIG. 1. The cumulative amount of drug permeated over 46 hours is shown in Table B below.

EXAMPLE 5

The hydrocortisone formulation K–P from Example 4 were tested in vitro for drug flux and compared with a commercial hydrocortisone cream, Dermolate® (0.5% hydrocortisone; Schering-Plough HealthCare Products; formulation "Der."), following the procedures of Example 3, except that the donor loading was 100 mg/1.13 cm² and the formulations were tested on each of two different samples of epidermis.

Figure 2:
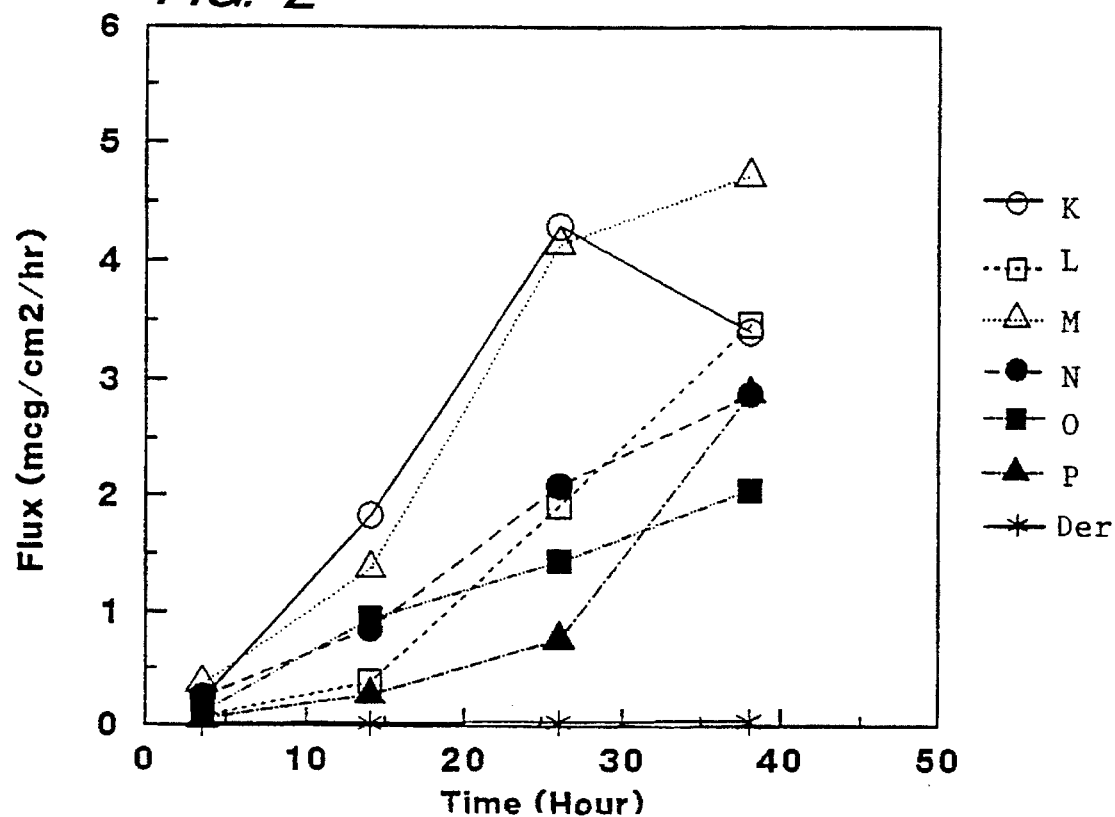
FIGS. 2 and 3 are graphs showing the flux of hydrocortisone through epidermis from various cream formulations falling under the present invention.
Figure 3:
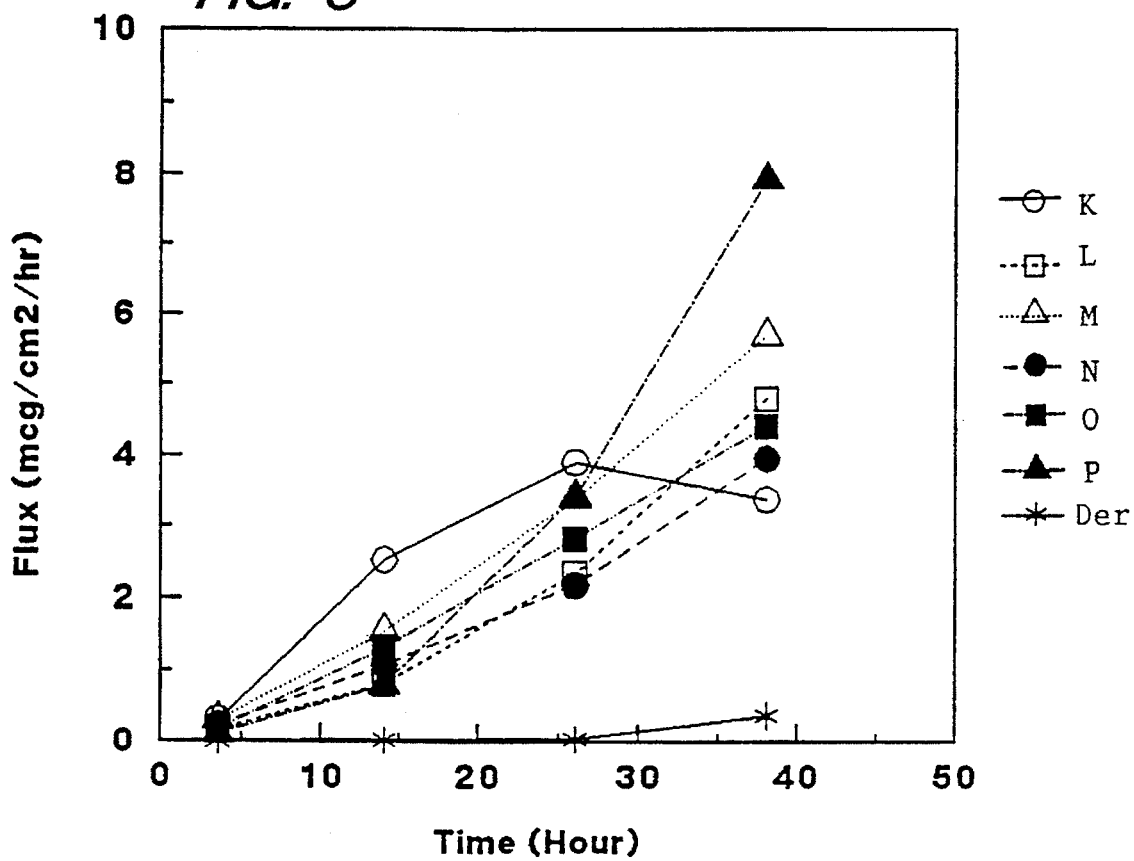

The transdermal flux of hydrocortisone through 1.13 cm² of epidermis #1 is shown in FIG. 2 and of epidermis #2 is shown in FIG. 3. The cumulative amount of drug permeated over 45 hours is shown in Table D below.

Dermolate, in addition to 0.5% hydrocortisone, also comprises ceteareth-30, cetearyl alcohol, mineral oil, petrolatum, propylene glycol, sodium phosphate and water.

TABLE D

| ID. | Cumulative HCT Permeated (µg/cm²/45 hr) | |
|---|---|---|
| | Epid. 1 | Epid. 2 |
| K | 118 | 125 |
| L | 74 | 105 |
| M | 130 | 137 |
| N | 75 | 93 |
| O | 56 | 111 |
| P | 51 | 158 |
| Der. | 1 | 10 |

EXAMPLE 6

Two hydrocortisone formulations according to the invention were prepared and tested in vivo for blanching response. A commercial hydrocortisone valerate cream, Westcort® (0.2% hydrocortisone valerate; Westwood-Squibb Pharmaceuticals), was also tested for comparison.

Two hydrocortisone cream formulations were prepared following the procedures of Example 1. Formulation Q had the following composition: glycerol monolaurate ("GML"; 25 wt %), sodium deoxycholate (1 wt %), white petrolatum (25 wt %), glycerol (12 wt %), hydrocortisone (0.5 wt %) and water (36.5 wt %). Formulation R was identical to Q except that it contained 25 wt % of glycerol monooleate ("GMO") rather than glycerol monolaurate.

Figure 4:
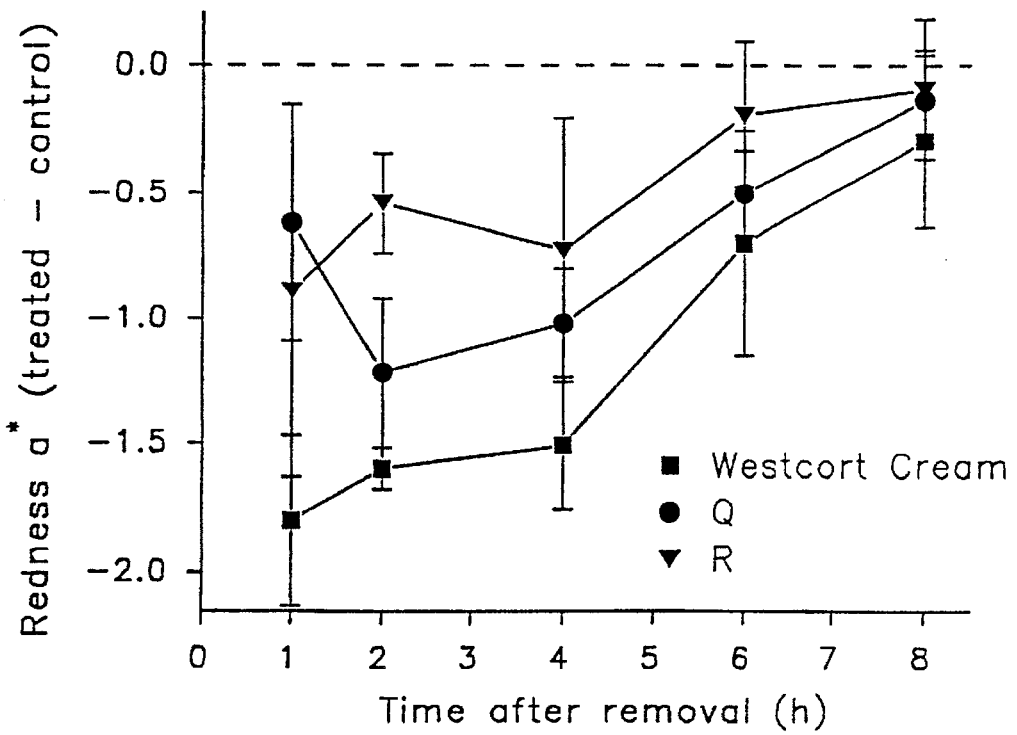
FIG. 4 is a graph showing the skin blanching (expressed as net value after substraction of the value recorded with untreated skin at a control site) obtained in the presence of two hydrocortisone formulations and a commercial formulation of hydrocortisone valerate.

Formulations Q and R, together with Westcort Cream, were tested in vivo in three adult males. For testing, 0.10 mL of each formulation was placed in an aluminum cup (1.1 cm²) and applied to the volar forearm of the subjects. After 16 hr, the cups were removed and the sites were washed. At various times thereafter, the sites were observed and the intensity of the vasoconstriction reaction was scored with an electronic instrument, the Minolta Chroma Meter. FIG. 4 illustrates the results, showing the skin blanching, expressed as net value (a* in the L*a*b* system) after substraction of the value recorded with untreated skin. Skin blanching was achieved with all three formulations. This reaction was more pronounced when GML was used as a permeation enhancer in place of GMO. The intensity and the persistence of the reaction with formulation Q containing hydrocortisone was only slightly less pronounced as compared to Westcort Cream containing hydrocortisone valerate, a more potent steroid than hydrocortisone.

Westcort cream, in addition to hydrocortisone valerate, contains white petrolatum, stearyl alcohol, propylene glycol, amphoteric-9, carbomer-940, sodium phosphate, sodium lauryl sulfate, sorbic acid and water.

The above description and examples have been given for ease of understanding only. No unnecessary limitations should be understood therefrom, as modifications will be obvious to those skilled in the art.

What is claimed is:

1. A formulation for the transdermal delivery of corticosteroid at a therapeutically effective rate to the skin of a host and with little or no irritation to the host, which formulation comprises:

(a) corticosteroid;

(b) 0.1–50 wt % of a hydrophobic permeation enhancer selected from the group consisting of glycerol monolaurate, glycerol monooleate, glycerol monolinoleate, sorbitan monolaurate, sorbitan dilaurate, sorbitan trilaurate, sorbitan monooleate, sorbitan dioleate, and sorbitan trioleate, the permeation enhancer being in microparticles of from about 0.01 to about 1000 microns in diameter;

(c) 0.1–5 wt % of a micronization stabilizer selected from the group consisting of sodium deoxycholate, sodium cholate, sodium dodecylsulfate, and sodium benzoate; and (d) an inert carrier.

2. A formulation according to claim 1 wherein the inert carrier is selected from the group consisting of water, glycerol, and polyethylene glycols.

3. A formulation according to claim 2 wherein the inert carrier is water.

4. A formulation according to claim 1 wherein the corticosteroid is hydrocortisone.

5. A formulation according to claim 1 wherein the permeation enhancer is selected from the group consisting of glycerol monolaurate, glycerol monooleate, and glycerol monolinoleate.

6. A formulation according to claim 1 which further comprises 10–60 wt % of a waxy oil and 5–25 wt % of a humectant.

7. A formulation according to claim 6 wherein the waxy oil is petrolatum and the humectant is glycerol.

* * * * *